United States Patent
Duraffourg et al.

(10) Patent No.: US 9,891,382 B2
(45) Date of Patent: Feb. 13, 2018

(54) OPTOMECHANICAL DEVICE WITH MECHANICAL ELEMENTS AND OPTICAL FILTERS FOR ACTUATING AND/OR DETECTING THE MOVEMENT OF THE ELEMENTS

(71) Applicants: COMMISSARIAT A L'ENERGIE ATOMIQUE ET AUX ENERGIES ALTERNATIVES, Paris (FR); CALIFORNIA INSTITUTE OF TECHNOLOGY, Pasadena, CA (US)

(72) Inventors: Laurent Duraffourg, Voiron (FR); Sebastien Hentz, Seyssinet-Pariset (FR); Mickael Lee Roukes, Pasadena, CA (US)

(73) Assignees: Commissariat à l'énergie atomique et aux énergies alternatives, Paris (FR); California Institute of Technology, Pasadena, CA (US)

( * ) Notice: Subject to any disclaimer, the term of this patent is extended or adjusted under 35 U.S.C. 154(b) by 0 days.

(21) Appl. No.: 15/031,198

(22) PCT Filed: Oct. 21, 2014

(86) PCT No.: PCT/EP2014/072483
§ 371 (c)(1),
(2) Date: Apr. 21, 2016

(87) PCT Pub. No.: WO2015/059109
PCT Pub. Date: Apr. 30, 2015

(65) Prior Publication Data
US 2016/0246000 A1    Aug. 25, 2016

(30) Foreign Application Priority Data

Oct. 22, 2013   (WO) .................. PCT/IB2013/003158

(51) Int. Cl.
*G02B 6/26*   (2006.01)
*G02B 6/12*   (2006.01)
(Continued)

(52) U.S. Cl.
CPC ..... *G02B 6/12007* (2013.01); *G01D 5/35312* (2013.01); *G01G 3/165* (2013.01);
(Continued)

(58) Field of Classification Search
USPC ...................................... 385/3, 39
See application file for complete search history.

(56) References Cited

U.S. PATENT DOCUMENTS 6,665,476 B2 * 12/2003 Braun ............... G02B 6/12002
                                                          385/14
6,909,824 B1   6/2005 Messica et al.
(Continued)

FOREIGN PATENT DOCUMENTS

WO   2011/154363 A2   12/2011
WO   2012/034949 A1   3/2012
(Continued)

OTHER PUBLICATIONS

L. J. Kauppinen, et al., "Micromechanically tuned ring resonator in silicon on insulator," Optical Society of America, Optics Letters, vol. 36, No. 7, Apr. 1, 2011, pp. 1047-1049, XP-001561562.
(Continued)

*Primary Examiner* — Eric Wong
(74) *Attorney, Agent, or Firm* — Oblon, McClelland, Maier & Neustadt, L.L.P.

(57) ABSTRACT

An optomechanical device with mechanical elements and optical filters for actuating and/or detecting movement of the elements, including a support, and on the support: an array of mechanical elements anchored to the support and configured to move with respect thereto, and an actuating and/or
(Continued)

detection device actuating the elements and/or detecting movement of the elements or frequency variations of the movement. The actuating and/or detection device includes an array of optical filters. Each filter resonates at a particular wavelength and is coupled to one of the elements. The actuating and/or detecting device is positioned in vicinity of all or some of the elements, between the elements and the support. The optical filters are fixed with respect to the support and the mechanical elements and the optical filters are superimposed.

12 Claims, 10 Drawing Sheets

(51) Int. Cl.
  *G01D 5/353* (2006.01)
  *G02B 6/35* (2006.01)
  *G01G 3/16* (2006.01)
  *G02B 6/122* (2006.01)
  *G01H 9/00* (2006.01)
  *G01D 5/26* (2006.01)
  *G02B 6/293* (2006.01)
  *G01N 15/10* (2006.01)

(52) U.S. Cl.
  CPC ....... *G02B 6/1225* (2013.01); *G02B 6/29343* (2013.01); *G02B 6/3536* (2013.01); *G01D 5/266* (2013.01); *G01D 5/268* (2013.01); *G01H 9/00* (2013.01); *G01N 2015/1043* (2013.01); *G02B 6/29395* (2013.01)

(56) References Cited

U.S. PATENT DOCUMENTS

| | | | | |
|---|---|---|---|---|
| 7,323,952 | B2* | 1/2008 | Pan | H03H 3/0077 333/186 |
| 8,669,823 | B1* | 3/2014 | Olsson | H03B 5/30 331/154 |
| 2006/0222292 | A1 | 10/2006 | Spoonhower et al. | |
| 2010/0265504 | A1* | 10/2010 | Kopp | G02B 6/12002 356/364 |
| 2012/0063717 | A1 | 3/2012 | Grenouillet et al. | |
| 2013/0170517 | A1* | 7/2013 | Duraffourg | G01J 5/02 374/121 |
| 2014/0283601 | A1* | 9/2014 | Bhave | G01P 15/093 73/504.12 |
| 2014/0313559 | A1* | 10/2014 | Lipson | G02B 6/29338 359/238 |

FOREIGN PATENT DOCUMENTS

| | | |
|---|---|---|
| WO | 2012/034951 A1 | 3/2012 |
| WO | 2012/034990 A1 | 3/2012 |

OTHER PUBLICATIONS

R. Rekha, et al., "Design of MOEM Vibration Sensor Using Optical MicroRing Resonator and MicroCantilever Beam," IEEE, TENCON 2011—2011 IEEE Region 10 Conference, pp. 747-751.
N. Yazdi, et al., "Micromachined Inertial Sensors," Proceedings of the IEEE, vol. 86, No. 8, Aug. 1998, pp. 1640-1659.
P. Waggoner, et al., "Micro- and nanomechanical sensors for environmental, chemical, and biological detection," The Royal Society of Chemistry, Lab Chip, vol. 7, 2007, pp. 1238-1255.
I. Bargatin, et al., "Large-Scale Integration of Nanoelectromechanical Systems for Gas Sensing Applications," American Chemical Society, Nano Letters, vol. 12, 2012, pp. 1269-1274.
M. S. Hanay, et al., "Single-protein nanomechanical mass spectrometry in real time," Nature Nanotechnology, vol. 7, Sep. 2012, pp. 602-608.
B. Mesgarzadeh, et al., "A Low-Noise Readout Circuit in 0.35-μm CMOS for Low-Cost Uncooled FPA Infrared Network Camera," Proc. of SPIE, vol. 7298, 2009, 8 pages.
T. Sakurai, "Solving Issues of Integrated Circuits by 3D-Stacking: Meeting with the era of power, integrity attackers and NRE explosion and a bit of future," ESSCIRC 2008—34$^{th}$ European Solid-State Circuits Conference, 7 pages.
M. Li, et al., "Harnessing optical forces in integrated photonic circuits," Nature, vol. 456, Nov. 27, 2008, pp. 480-485.
C. J. Barrelet, et al., "Hybrid Single-Nanowire Photonic Crystal and Microresonator Structures," American Chemical Society, Nano Letters, vol. 6, No. 1, 2006, pp. 11-15.
D. Van Thourhout, et al., "Optomechanical device actuation through the optical gradient force," Nature Photonics, vol. 4, Apr. 2010, pp. 211-217.
J. Ma, et al., "Applications of optomechanical effects for on-chip manipulation of light signals," Current Opinion in Solid State and Materials Science, vol. 16, 2012, pp. 82-90.
G. Anetsberger, et al., "Near-field cavity optomechanics with nanomechanical oscillators," Nature Physics, vol. 5, Dec. 2009, pp. 909-914.
M. Eichenfield, et al., "Actuation of micro-optomechanical systems via cavity-enhanced optical dipole forces," Nature Photonics, vol. 1, Jul. 2007, pp. 416-422.
J. Sun, et al., "Large-scale nanophotonic phased array," Nature, vol. 493, Jan. 10, 2013, pp. 195-199.
P. Robert, et al., "M&NEMS: A new approach for ultra-low cost 3D inertial sensor," IEEE, IEEE Sensors 2009 Conference, pp. 963-966.
I. Bargatin, et al., "Sensitive detection of nanomechanical motion using piezoresistive signal downmixing," American Institute of Physics, Applied Physics Letters, vol. 86, 2005, 3 pages.
International Search Report and Written Opinion of the International Searching Authority dated Dec. 2, 2014 in PCT/EP2014/072483 Filed Oct. 21, 2014.

\* cited by examiner

OPTOMECHANICAL DEVICE WITH MECHANICAL ELEMENTS AND OPTICAL FILTERS FOR ACTUATING AND/OR DETECTING THE MOVEMENT OF THE ELEMENTS

TECHNICAL FIELD

The present invention relates to an optomechanical device comprising an array of mechanical elements and a device for actuating and/or detecting the movement of the mechanical elements.

The invention in particular applies to the actuation and detection of the movement of a MEMS or NEMS array, by optomechanical coupling in a three-dimensional configuration.

It will be recalled that MEMS are micro-electromechanical systems, and NEMS are nano-electromechanical systems.

More generally, the invention applies to all types of sensors (physical, chemical or biological sensors), in particular mass sensors and gas sensors.

BACKGROUND OF THE INVENTION

Devices with resonant beams are already known from the following documents:
WO 2012/034949, invention by S. Hentz,
WO 2012/034951, invention by S. Hentz et al.,
WO 2012/034990, invention by S. Hentz.

MEMS and NEMS are commonly used as inertial sensors. On this subject, reference may be made to the following document:
N. Yazdi et al. (1998). Micromachined Inertial Sensors, 86(8).

They are also used as mass sensors (for gases, for example). On this subject, reference may be made to the following document:
P. S. Waggoner et al. (2007). Micro- and nanomechanical sensors for environmental, chemical, and biological detection. *Lab on a chip,* 7(10), 1238-55.

New applications, such as infrared flow measurement or mass measurement, require the use of a plurality of MEMS or NEMS sensors (in particular due to the increase in the capture or redundancy surface). On this subject, reference may be made to the following documents:
US 2013/0170517, Bolometer having frequency detection, invention by L. Duraffourg et al.
I. Bargatin et al. (2012). Large-scale integration of nano-electromechanical systems for gas sensing applications. *Nano letters,* 12(3), 1269-74.
M. S. Hanay et al. (2012). Single-protein nanomechanical mass spectrometry in real time. *Nature Nanotechnology,* 7(9), 602-608.

Today, M/NEMS arrays are primarily addressed, read and actuated electrically. Reading circuits that are close to those of imagers have for example been presented—see the following document:
B. Mesgarzadeh et al. (2009). A low-noise readout circuit in 0.35-μm CMOS for low-cost uncooled FPA infrared network camera. *Proceedings of SPIE,* 7298, 72982F-72982F-8.

Three-dimensional solutions have also already been proposed—see the following documents:
WO 2011/154363, invention by T. Ernst et al.
T. Sakurai (2008). Solving issues of integrated circuits by 3D-stacking Meeting with the era of power, integrity attackers and NRE explosion and a bit of future. *ESSCIRC 2008—34th European Solid-State Circuits Conference,* 10-16.

When the size of the arrays becomes very considerable, the addressing and reading strategies become very complex from the system perspective (complex reading mode in order to be able to address many pixels without excessively deteriorating the detection performance of the sensors, for example) as well as the technology perspective (density of the interconnections, for example).

BRIEF DESCRIPTION OF THE INVENTION

The present invention aims to resolve the aforementioned drawbacks.

To that end, according to one aspect of the invention, new architectures for actuating and detecting arrays of mechanical elements such as MEMS or NEMS are used, said architectures integrating at least one photonic circuit.

Specifically, the invention relates to an optomechanical device comprising:
a support, and thereon:
an array of mechanical elements that are anchored to the support and capable of moving with respect thereto, and
an actuating and/or detection device, for actuating the mechanical elements and/or detecting the movement of the mechanical elements or frequency variations of the movement,
the optomechanical device being characterized in that the actuating and/or detection device comprises a photonic circuit including an array of optical filters, the number of which is less than or equal to the number of mechanical elements, each optical filter resonating at a particular wavelength and being optically coupled to one of the mechanical elements to actuate them and/or detect the movement or the frequency variation of the movement of the elements independently of one another, the actuating and/or detecting device being positioned in the vicinity of all or some of the mechanical elements, between the latter and the support, wherein the optical filters are fixed with respect to the support and wherein the mechanical elements and the optical filters are superimposed.

Using a particular wavelength for each optical filter makes it possible to perform addressing of the mechanical elements. Thus, each position of a chemical element in the array has a corresponding given wavelength.

The structure of the device covered by the invention is of the three-dimensional type.

According to a preferred embodiment of the optomechanical device of the invention, each mechanical element has at least two ends which are anchored to the support.

According to a preferred embodiment of the present invention, the actuating and/or detecting device is positioned below or above all or some of the mechanical elements, between the latter and the support.

According to one particular embodiment of the optomechanical device covered by the invention, the optical filters are optical resonators. These optical resonators may be chosen from among annular optical resonators, discoid optical resonators and photonic crystals.

According to one particular embodiment of the invention, the photonic circuit further includes at least one optical waveguide that extends across from the optical resonators and is placed at a small enough distance therefrom to allow optical interactions between them. This distance is preferably comprised in the interval from 10 nm to 1 µm.

According to one particular embodiment of the invention, the actuating and/or detection device comprises a device for electrical actuation of the mechanical elements.

The mechanical elements may be suspended elements that may or may not be actuated. These elements may be resonated. They may be chosen from among cantilevers, bi-embedded beams, plates or discs. The sections of the beams may be variable (variable width, or even variable thickness, along the considered beam).

According to one particular embodiment of the optomechanical device covered by the invention, each mechanical element comprises a substantially rectilinear beam, perpendicular to the support and having first and second ends, the first end being anchored to the support. There are many possibilities for attaching the beam to its support: "rigid" embedding or "flexible" embedding.

The second end of the beam may be provided with a substantially planar plate, perpendicular to the beam and forming a receiving area.

BRIEF DESCRIPTION OF THE DRAWINGS

The present invention will be better understood upon reading the description of example embodiments provided below, purely for information and non-limitingly, in reference to the appended drawings, in which.

DETAILED DESCRIPTION OF THE INVENTION

In the invention, mechanical systems such as MEMS or NEMS are coupled to a photonic system making it possible to perform the transducer function (actuating each micro/nano structure and detecting its movement). It should be noted that devices according to the invention are different from the traditional so-called MOEMS systems, which are MEMS performing optical functions such as:

moving a micro-mirror (for example, a scanner or projector) or adding/removing optical channels (wavelength channels) in a telecommunications system.

In the case at hand, a suspended structure such as a beam is set in motion by an optical force. To that end, it suffices to place the structure near an optical waveguide in which the light is guided. Even if the optical energy is confined inside the guide, a small portion of the wave, called "evanescent wave", "overflows" on the sides of the guide. By placing the mechanical structure in the area of influence of said evanescent wave, which may go from several hundred nanometers to 10 nm, the MEMS or NEMS undergoes an optical force that results from the gradient of the electromechanical field. This optical force depends, nonlinearly, on the interval separating the waveguide from the structure and is proportional to the optical power injected in the waveguide. This guide may be a simple rectilinear guide or an optical resonator of the resonant ring type or a photonic crystal. On this subject, reference may be made to the following documents:

M. Li et al. (2008). Harnessing optical forces in integrated photonic circuits. *Nature,* 456(7221), 480-4.

C. J. Barrelet et al. (2006). Hybrid single-nanowire photonic crystal and micro-resonator structures. *Nano letters,* 6(1), 11-5.

For an overview of the different known techniques and different known optomechanical components, reference may be made to the following documents:

D. Van Thourhout et al. (2010). Optomechanical device actuation through the optical gradient force. *Nature Photonics,* 4(4), 211-217.

J. Ma et al. (2012). Applications of optomechanical effects for on-chip manipulation of light signals. *Current Opinion in Solid-State and Materials Science,* 16(2), 82-90.

The movement of the NEMS or MEMS causes a variation in the distance that separates it from the waveguide. This variation in the distance results in modulating the intensity of the beam propagating in the guide. This is the inverse phenomenon from that in play in optical actuation. The evanescent wave is more or less disrupted by the movement of the NEMS or MEMS that is placed in its area of influence. This is a near optical field effect.

It is interesting to use coupling between the NEMS or MEMS and an optical resonator such as a disc-shaped resonator, a ring-ship resonator or a photonic crystal.

Such a resonator is similar to a Fabry-Pérot resonator. In that case, the aforementioned distance variation has two effects.

modulation of the optical coupling—the intensity of the waves is then modulated as a function of the interval between the resonator and the NEMS or MEMS (in strong coupling mode), and modulation of the optical frequency of the resonator (equivalently, modulation of the phase of the optical signal).

The phase modulation, caused by the movement of the MEMS or NEMS, is present even in case of weak coupling between the optical waveguide and the MEMS or NEMS. The measurement of the transmitted light intensity therefore constitutes an optical detection means. This detection principle is for example known from the following documents, to which reference may be made:

G. Anetsberger et al. (2009). Near-field cavity optomechanics with nanomechanical oscillators. *Nature Physics*, 5(12), 909-914.

M. Eichenfield et al. (2007). Actuation of micro-optomechanical systems via cavity-enhanced optical dipole forces. *Nature Photonics*, 1(7), 416-422.

It will be recalled that a Fabry-Pérot interferometer includes two opposite planar mirrors, separated by a given distance and forming an optical resonator with a high quality factor Q. The optical cavity resulting therefrom behaves like an optical filter only selecting certain internal propagation modes. These resonant optical modes are separated by a free spectral interval FSI and have a spectral width δv. The quality of the resonator thus obtained is characterized by its spectral fineness F=FSI/δv. The latter is related to the quality factor Q=$v_0$/δv, where $v_0$ represents the frequency corresponding to the central wavelength of an optical mode of the cavity.

Figure 1:
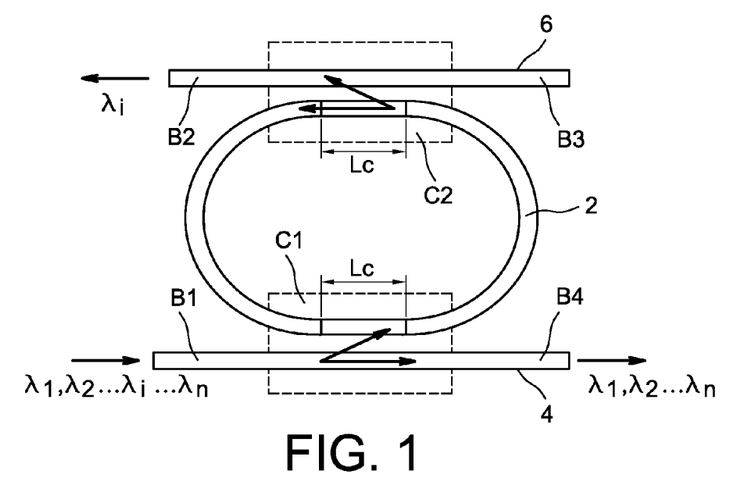
FIG. 1 is a diagrammatic top view of a ring-shaped optical resonator.

FIG. 1 is a diagrammatic view of a ring-shaped optical resonator 2. In the illustrated example, two optical, rectilinear and parallel waveguides 4 and 6 are placed on either side of the ring 2. The operating principle is the following:

When light is injected into the ring-shaped optical waveguide, that light rotates in the guide quite similarly to the light going back and forth in a Fabry-Pérot resonator.

This ring therefore constitutes an optical resonator only guiding the optical modes having specific frequencies inversely proportional to its length, with a free spectral interval FSI that depends not only on the perimeter 2πR of the ring, but also the coupling lengths Lc on which the straight waveguides 4 and 6 address the ring 2.

Incident light is sent into one end B1 of the guide 4. If the incident light has a wide spectrum (set of wavelengths $\lambda_1$, $\lambda_2 \ldots \lambda_i \ldots \lambda_n$), the ring will only select the wavelength $\lambda_i$ corresponding to its specific wavelength (or specific resonance frequency). The light with wavelength $\lambda_i$ exits the guide 6 through one end B2 thereof. Its other end is denoted B3. The non-selected lights leave the guide 4 through the other end B4 thereof. The fineness F, where $$F = \frac{\pi\sqrt{\alpha|t1t2|}}{1-\alpha|t1t2|},$$

is similar to that of a Fabry-Pérot resonator. It in fact depends on the attenuation coefficient α of the ring-shaped waveguide and the transmission rates t1 and t2 of the couplers C1 and C2, which are formed by the guide 4 and the ring 2 and by the guide 6 and said ring 2, respectively.

Below, we will consider different aspects of the present invention.

This involves actuating and/or detecting all or part of an array of mechanical elements such as MEMS or NEMS, and advantageously reading and/or actuating each pixel formed by one or more MEMS or NEMS, using a photonic circuit that contains all of the necessary waveguides, using a three-dimensional architecture.

Figure 2:
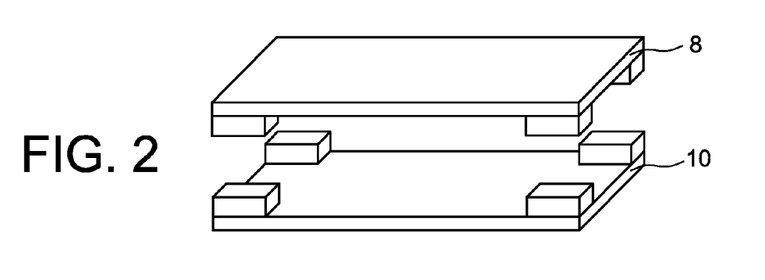
FIG. 2 is a very diagrammatically illustration of an example three-dimensional architecture, relative to a device according to the invention, FIGS. 3A to 3C diagrammatically illustrate the principle of reading and actuating a MEMS or NEMS array using a photonic circuit placed below the MEMS or NEMS array.

FIG. 2 diagrammatically illustrates one example of a three-dimensional architecture showing the stack of two planes 8 and 10. The first plane 8 is made up of the array of MEMS or NEMS, and the second plane 10 is formed by an addressing and optical actuating/detection circuit.

Each MEMS or NEMS is placed in an area of influence (near field) of the waveguide of the photonic circuit. "Area of influence" refers to a small enough separation difference for the optical force to be capable of actuating the microstructure or nanostructure to obtain movements of approximately from 1 nm to 100 nm. This separating distance is advantageously comprised between 10 nm and 1 μm. The plane 8 of the MEMS or NEMS is placed above the plane 10 containing the optical arrays. With such a separation distance, it is also possible to perform the optical detection of the movement of each pixel.

Figure 3A:
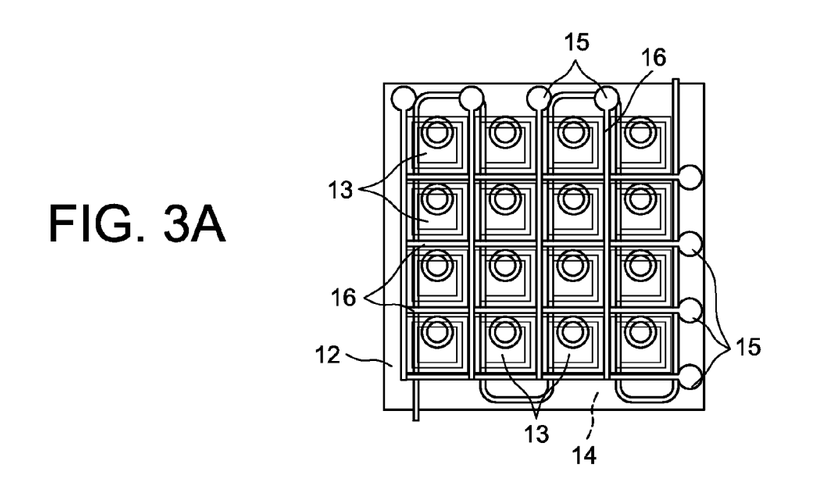
Figure 3B:
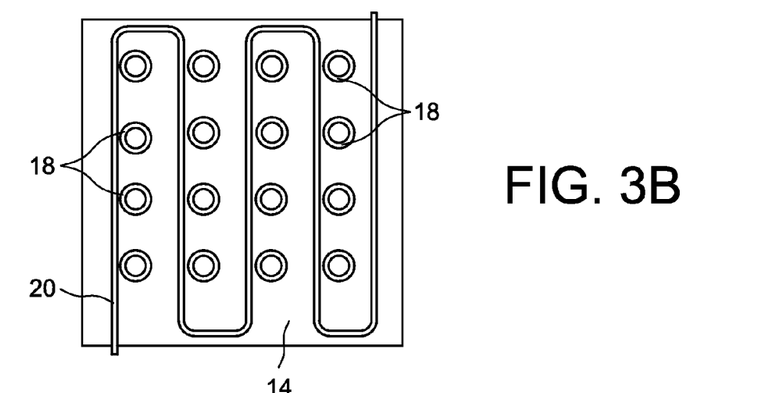
Figure 3C:
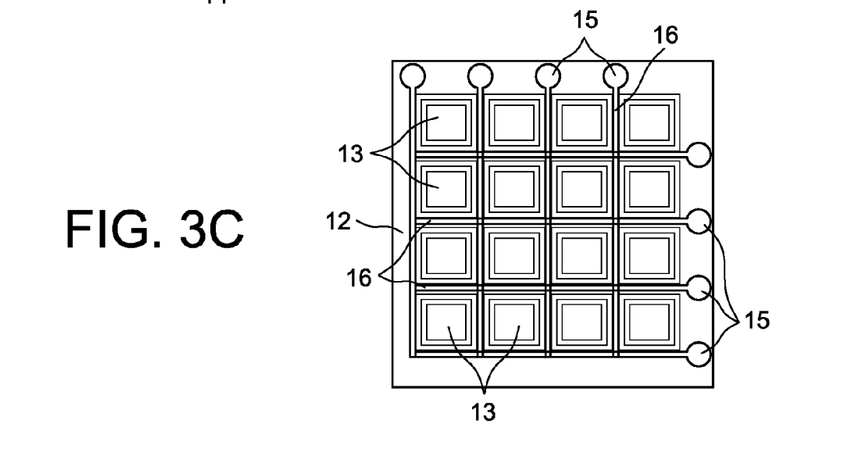

FIGS. 3A to 3C diagrammatically illustrate the principle of reading and actuating a MEMS or NEMS array optically using a photonic circuit integrated into that array and placed below it. The detection is used optically. The actuation may be done optically or electrically.

In the case of these figures, not only is each of the MEMS or NEMS of the array addressed by frequency multiplexing, but they are also actuated independently of one another.

FIG. 3A is a diagrammatic top view of two superimposed chips, namely a chip 12 bearing the MEMS or NEMS 13 and assumed to be transparent (solely for comprehension of the drawing), and an optical chip 14. We also see the interconnections 15 for the actuating electrodes 16 in the event one wishes to use electrical actuation. In the described example, at least two ends of each MEMS or NEMS 13 are anchored to chip 12.

FIG. 3B is a diagrammatic top view of the optical chip 14 bearing an array of ring-shaped resonators 18 and an optical waveguide 20 that somewhat forms undulations to extend along each row of the array of resonators, as shown. Resonators 18 are fixed with respect to the optical chip 14.

FIG. 3C is a diagrammatic top view of the mechanical chip 12 bearing the MEMS or NEMS 13. One can again see the interconnections 15 and the electrodes 16.

The photonic circuit comprises an array of optical resonators (advantageously discs or optical rings made from silicon), respectively placed below the mechanical pixels to be addressed. Purely for information and non-limitingly, the arrangement of such an array may resemble the array of photonic antennas described in the following document:

J. Sun et al., (2013). Large-scale nano photonic phased array. *Nature*, 493(7431), 195-9.

Each optical resonator is not only a transduction element (for actuating and detection, as described above), but also a frequency addressing element. As seen above with respect to Fabry-Pérot resonators and ring-shaped optical resonators (FIG. 1), each optical resonator in fact has a specific optical resonance. The position of a mechanical pixel (NEMS or MEMS, or NEMS or MEMS group) in the array of mechanical elements may then be coded on the natural frequency of an optical resonator. It is then possible, by frequency multiplexing, to perform simultaneous addressing of all of the pixels of the array of mechanical elements one wishes to actuate and/or detect. It is necessary to use as many optical resonators as there are MEMS or NEMS to be addressed.

It should be noted that the MEMS or NEMS may be (mechanically) resonant or non resonant structures. Each of these structures may be a test mass in the case of an accelerometer. On this subject, reference may be made to the following document:

P. Robert et al. (2009). M & NEMS: A new approach for ultra-low cost 3D inertial sensor. *IEEE Sensors* (pp. 963-966).

This may also be a vibrating beam, for example in the case of a mass sensor. On this subject, reference will be made to the aforementioned article by I. Bargatin et al. (2012).

This may also be a vibrating plate of the type used in certain resonant microbolometers, for example those described in the aforementioned document US 2013/0170517, Bolometer having frequency detection.

Figure 4:
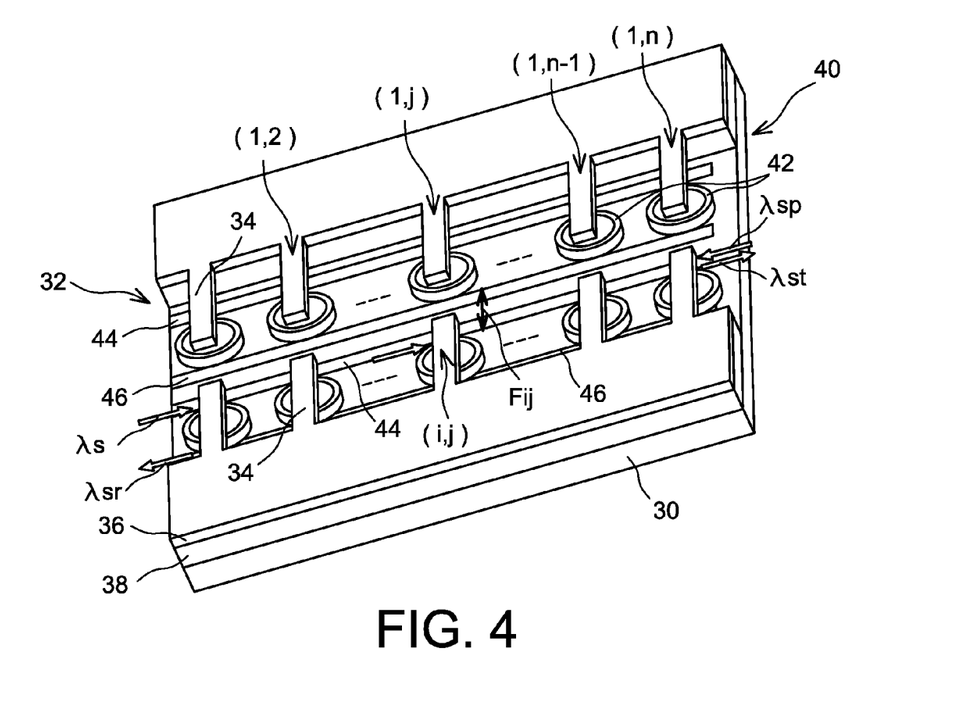
FIG. 4 is a diagrammatic perspective view of one example of the device covered by the invention.

FIG. 4 is a diagrammatic perspective view of one example of the optomechanical device covered by the invention. This optomechanical device comprises a support made up of a silicon substrate 30. It also comprises an array 32 of mechanical elements 34 that are anchored to the substrate 30 and able to move with respect thereto. In the example, these elements 34 are MEMS or NEMS, for example nanocantilevers. They are formed on an upper layer 36, for example made from silicon. This layer 36 rests on the substrate 30 by means of a sacrificial layer 38 for example made from silica. The optomechanical device also comprises an actuating interaction device 40, to actuate mechanical elements 34 and detect the movement of the mechanical elements or detect frequency variations of their movement.

According to the invention, the actuating and/or detection device 40 is a photonic circuit including an array of optical filters 42, the number of which is equal to the number of mechanical elements 34. Each optical filter 42 is fixed with respect to the substrate 30, resonates at a particular wavelength and is optically coupled to one of the mechanical elements 34. This makes it possible to actuate the latter and detect the movement or the frequency variation of the movement of the elements 34 independently of one another. As shown, the actuating and detection device is positioned in the vicinity of, preferably below or above, the mechanical elements 34, between the latter and the substrate 30.

The optical filters 42 are optical resonators, for example annular optical resonators.

As shown, the photonic circuit 40 further includes pairs of optical waveguides 44, 46, for example made from silicon, that extend along rows of optical resonators, on either side thereof, and which are placed at a small enough distance from those optical resonators, preferably from 10 nm to 1 µm, to allow an optical interaction between said resonators and said waveguides. The guides will be discussed again later.

Below, the operating principle of the device shown in FIG. 4 is explained.

All of the optical frequencies corresponding to all of the targeted mechanical pixels (or all of the targeted optical resonators) are sent into a same input waveguide 44.

This sending is symbolized by reference $\lambda s$ in FIG. 4, where $\lambda s$ represents the set of optical wavelengths $\lambda i1$, $\lambda i2$, ..., $\lambda ij$ ... $\lambda iM$ sent into the guide 44 of row i, M denoting the number of columns of the array 42.

The resonators may be dimensioned (regarding the radius in the case of a ring, or the radius of the holes and the pitch between the holes in the case of photonic crystals) so as to have different natural optical modes. (It is also possible to consider controlling the device by adding electrodes on either side of the resonant ring or below it, resulting in thermal control of the index of the silicon and control of the wavelength of the resonant optical mode. An electro-optical effect modulating the number of carriers (electrons or holes) contained in the guide also makes it possible to adjust the index. This method, however, remains too heavy to implement, in particular for an array).

Each resonator 42, corresponding to row i and column j, only selects the wavelength $\lambda ij$ associated with its natural resonance frequency. The corresponding natural resonance mode makes it possible to generate an optical force $F_{ij}$ actuating the MEMS or NEMS 34 numbered ij (or group of NEMS or MEMS).

The detection is done by means of the signals reflected by the optical resonators and noted $\lambda sr$ in FIG. 4. The movement $x_{ij}$ of the MEMS or NEMS numbered ij results in modulating the light intensity $I_{ij}$ of the optical wave with wavelength $\lambda ij$ (case of strong coupling). When the MEMS or NEMS are used as mechanical resonators (for mass detection), each output optical signal (reflected) is then modulated in terms of amplitude and frequency. These modulations depend on the modulation of the optical coupling caused by the movement of the MEMS or NEMS.

It is also possible to use two coherent light sources (for example, two laser diodes) at different wavelengths, so as to limit the cross-talk between the actuation and the detection: the first wavelength $\lambda p$ serves as pump signal (actuating signal) and the second wavelength $\lambda st$ serves as probe signal (detection signal). The light intensity of the pump signal is modulated at the resonance frequency of the MEMS or NEMS when the latter are mechanical resonators. The probe signal is also modulated at the same frequency (or a close frequency) so as to perform a homodyne or heterodyne detection of the signal.

In its simple form, the probe signal is not modulated, but is continuous. This probe signal will then be modulated by the movement of the MEMS or NEMS.

In a more complex embodiment, it is possible to modulate the probe signal (by phase, rather) so as to perform a heterodyne detection (see the description of FIG. 7 below).

It is specified that each optical resonator numbered ij has a different radius $R_{ij}$ from the others, which makes it possible to obtain an optical natural mode having a wavelength $\lambda ij$, that is different from the others. This wavelength $\lambda ij$ encodes the position of the MEMS or NEMS that is placed above the considered resonator. It is possible to detect the transmitted wavelengths or the reflected wavelengths, which makes it possible to limit the continuous background caused by the optical actuating signal. It should be noted that it is possible to send a set of pump wavelengths for actuating and to detect the movements of the MEMS or NEMS through another series of wavelengths, the signals being contra-propagative. In that case, the actuation is easily eliminated by optical filtering between the device (photonic network/MEMS or NEMS array assembly) and the detector.

The originality of the device shown in FIG. 4 lies in using the combination of optical force, near-field optical detection and optical addressing by wavelength multiplexing, using optical resonators, to measure the response of a NEMS or MEMS array. The wavelength multiplexing technique serves as an addressing technique for the MEMS or NEMS. This addressing is made possible by the optomechanical coupling, which modifies the natural wavelength of each optical resonator.

Figure 5:
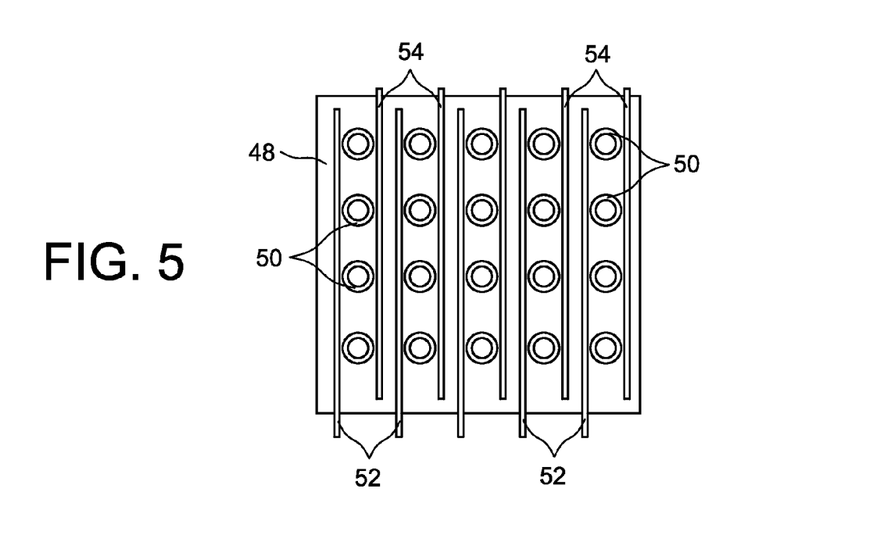
FIG. 5 is a diagrammatic top view of an optical circuit usable in the invention.

FIG. 5 is a diagrammatic top view of an optical chip, i.e., an optical circuit 48, usable in the present invention. The optical resonators here bear reference 50. Each resonator row is framed by two optical waveguides, namely an actuating waveguide 52 for the optical inputs and a detection waveguide 54 for the optical outputs. Thus, the optical signal is read on a different waveguide so as to separate actuation and detection and thereby limit cross-talk.

Figure 6:
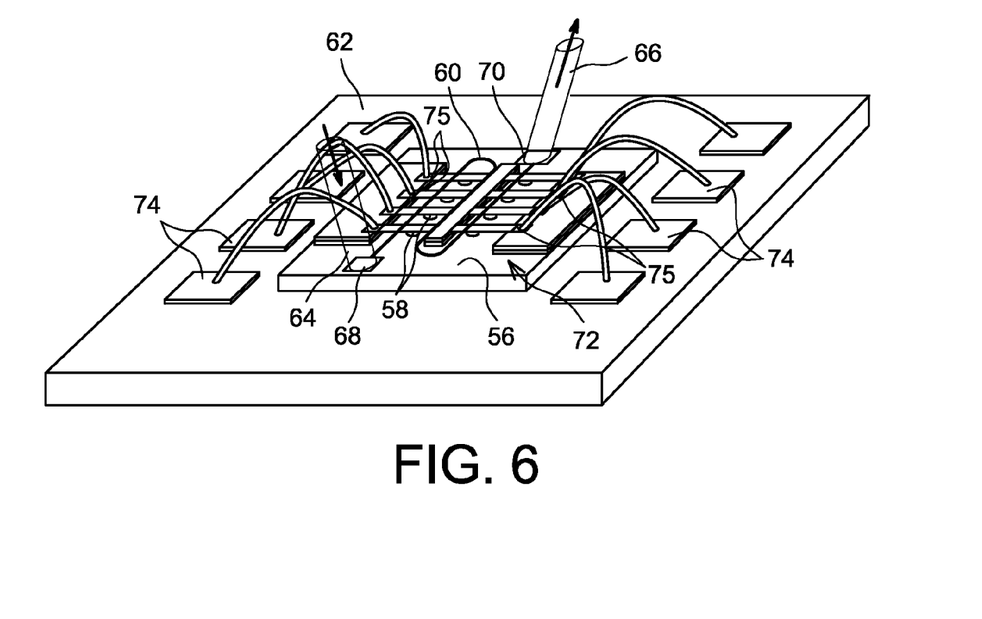
FIG. 6 is a partial diagrammatic perspective view of one example of the device covered by the invention, FIG. 7 diagrammatically illustrates an example system for reading and actuating a MEMS or NEMS in one example of the invention, FIGS. 8A to 8J diagrammatically illustrate the steps of a method for manufacturing a device according to the invention, FIGS. 9A to 9E diagrammatically illustrate the steps of another method for manufacturing a device according to the invention.

FIG. 6 is a diagrammatic partial perspective view of one example of an optomechanical device according to the invention. It shows a chip 56 bearing the optical circuit. The fixed optical resonators bear reference 58. An optical waveguide 60 extends between the rows of resonators as in the case of FIG. 3B. The chip 56 rests on a printed circuit board 62. Two optical fibers 64 and 66 are respectively connected to the two ends of the waveguide 60 by means of coupling Bragg gratings 68 and 70. The fibers 64 makes it possible to inject the light coming from an external laser source (not shown) into the guide 60. The fiber 66 makes it possible to recover the light coming from the guide 60 to send it into an external circuit (not shown) comprising an optical amplifier, an optical demultiplexer and a photodetector at each output of the demultiplexer.

It also shows the array 72 of the MEMS or NEMS that is positioned above the optical circuit. It additionally shows the electrical connections 74 designed for optional electrical actuation of the MEMS or NEMS, namely, thermoelastic actuation in the example, done using suitable electrodes 75.

Let us return to FIG. 4.

The detected signals are optically filtered, amplified, for example using an erbium-doped fiber amplifier, and demultiplexed. For arrays of MEMS or NEMS mechanical resonators, it is also interesting to perform synchronous detection by amplitude- or phase-modulating the detection signal, or probe signal, at the same frequency as the excitation signal, or pump signal, which corresponds to the resonance frequency of the MEMS or NEMS or a slightly offset frequency. This heterodyning technique, consisting of modulating the probe signal at a slightly different frequency, further makes it possible to work at a low frequency while eliminating the continuous background and eliminating the low-frequency noise. On this subject, reference will be made to the following document:

I. Bargatin et al. (2005). Sensitive detection of nanomechanical motion using piezoresistive signal downmixing. *Applied Physics Letters*, 86(13), 133109.

Figure 7:
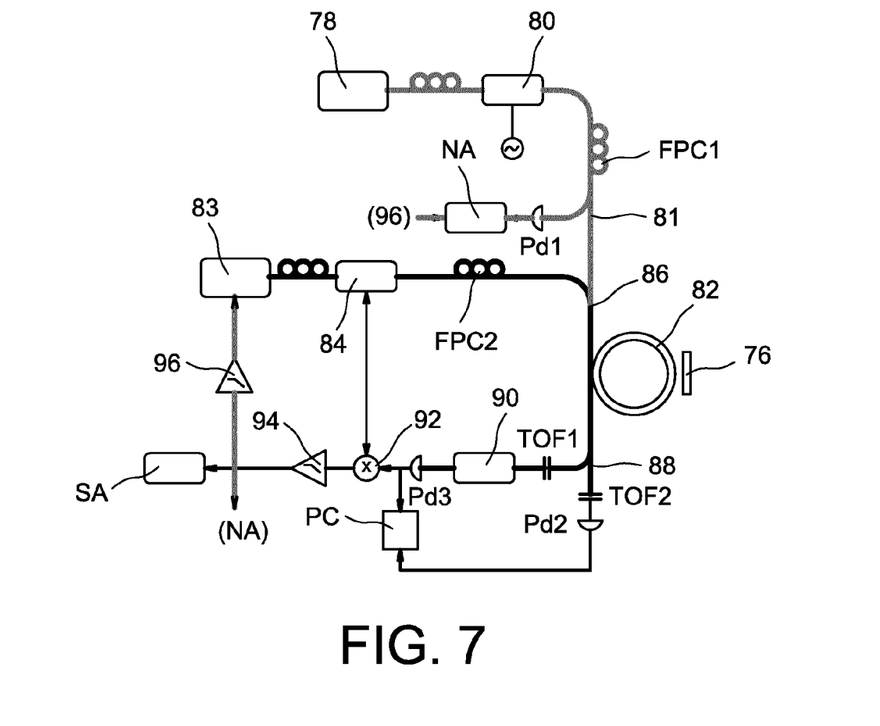

FIG. 7, briefly described below, diagrammatically illustrates one example of a system making it possible both to read and actuate a MEMS or NEMS mechanical element 76.

A laser source 78 (1530 nm) is intensity-modulated by the intensity modulator 80 and emits a light transported by an optical waveguide 81 and making it possible to actuate the element 76 using the ring-shaped resonator 82. Reference FPC1 designates a first polarization controller. Reference Pd1 designates a photodetector intended to detect the modulated signal. The signal corresponds to the optical intensity coming from the phase-modulated signal, reflected by the optical cavity whereof the response itself is modulated by the movement of the MEMS or NEMS (see explanation provided regarding the modulation of the coupling between the waveguide and the MEMS or NEMS).

Reference NA designates an optional network analyzer. A phase-modulated laser source 83 (1560 nm) provides a probe signal to detect the movement of the element 76. A phase modulator 84 allows both a heterodyne detection of the signal and a stabilization of the probe laser (Pound-Drever-Hall technique). In the example shown in FIG. 7, the movement of the resonant MEMS or NEMS causes a variation in the natural optical mode of the resonant cavity and therefore the light intensity reflected/filtered by the optical cavity.

Reference FPC2 designates a second polarization controller and reference 86 designates a 50/50 coupler. Reference 88 designates a 90/10 coupler. Reference 90 designates an erbium-doped fiber amplifier. Reference TOF1 designates an optical filter making it possible to select the signal around the probe wavelength. Reference TOF2 designates an optical filter making it possible to select the signal around the pump wavelengths. References Pd2 and Pd3 designate photodetectors. Reference PC designates a computer for processing the information. Reference 92 designates an electric mixer (multiplying two signals) in order to perform the heterodyning. References 94 and 96 designate low pass filters to select only the modulation frequency. Reference SA designates a spectrum analyzer (optional).

The optical waveguides essentially have a very wide bandwidth that is much greater than 1 GHz (with respect to electric multiplexing). It is therefore possible to obtain simultaneous addressing, by wavelength multiplexing, of a large MEMS or NEMS matrix.

To increase the number of pixels, it is possible to combine wavelength multiplexing with time multiplexing. For example, for a matrix M×N, a MEMS or NEMS column of rank j is addressed simultaneously by wavelength multiplexing, and the M rows are swept by time multiplexing.

It should be noted that the MEMS or NEMS can be actuated using electrical means that may or may not be integrated into the chip (electrostatic, piezoelectric, thermal actuation, for example), the detection remaining optical.

Each NEMS or MEMS may bear one of the two arms of the corresponding coupler. However, it may also constitute one of the arms of the coupler. The movement of the NEMS or MEMS causes modulation of the coupling.

In the invention, the mechanical elements may be in the form of discs, plates, or membranes, for example.

The optical sources, which are necessary for operation of the optomechanical device, may be attached on the photonic part of that device. And, the photodetectors necessary for the operation may be integrated or attached in said photonic part.

The MEMS or NEMS may have various sizes. Purely for information and non-limitingly, they have a typical length from 10 $\mu$m to 500 nm, a width from 1 $\mu$m to 10 nm, and a thickness from 200 nm to 10 nm.

Below, we consider the manufacture of devices according to the invention.

The waveguides may be made from silicon or silicon nitride on a rigid support, for example a silicon plate. It is also possible to produce the photonic circuit on a flexible substrate, with polymer optical waveguides.

The MEMS or NEMS that can be used in the invention may be made from silicon, silicon nitride, silica, silicon carbide, or any other material, even polymer. The suspended structures are preferably made from silicon, silicon nitride or silicon carbide.

I. First Example of Manufacturing Method (FIGS. 8A to 8J).

Figure 8A:
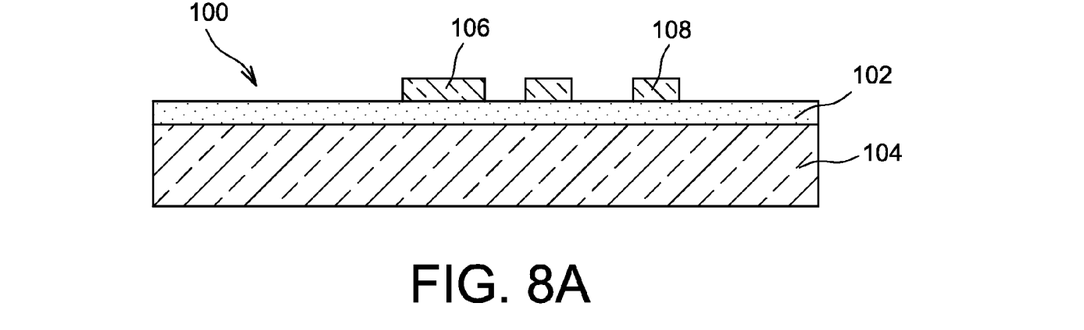

I.1 Manufacture of the Photonic Wafer (FIG. 8A)

To manufacture the device, one starts with a BOX (buried oxide) plate 100 comprising a layer of silica 102 that is 200 nm thick on a silicon substrate 104. It is structured to obtain the desired photonic circuits (standard process). Each waveguide 106 is made from silicon and has a section from approximately 100×100 nm$^2$ to 500×500 nm$^2$, for example. Each ring-shaped optical resonator 108 has an inner radius of approximately from 5 $\mu$m to 20 $\mu$m, a width of approximately from 200 nm to 500 nm, and a thickness of approximately from 200 nm to 500 nm. The typical lengths of the intra-chip waveguides will be approximately from 100 $\mu$m to a few millimeters.

On this subject, reference may for example be made to the following documents.

US 2012/0063717, Method of producing a photonic device and corresponding photonic device, invention by Laurent Grenouillet et al.

US 2010/0265504, Optical device with superimposed photonic circuits for coupling to one or more optical waveguides, invention by Christophe Kopp et al.

Figure 8B:
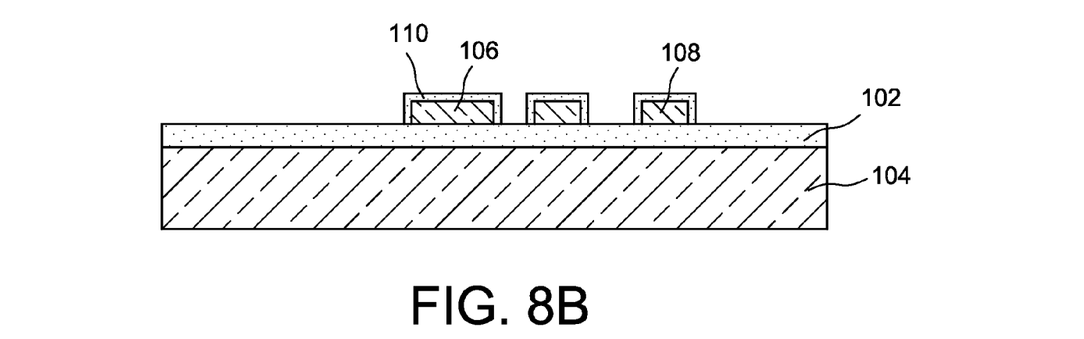
Figure 8C:
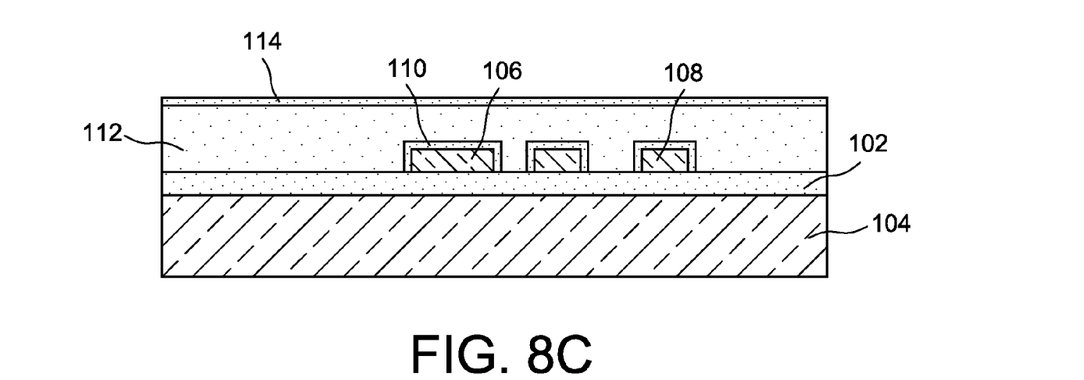

I.2 Preparation/Protection of the Wafer (FIGS. 8B and 8C)

A fine layer of oxide 110 is deposited to protect the silicon optical waveguide, for example by PECVD. The thickness of this layer 110 is for example 10 nm.

A sacrificial polysilicon layer 112 is next deposited, over a height greater than 500 nm. This height is for example 550 nm to leave, upon final release, a space of 50 nm between the MEMS or NEMS used and the waveguide. (Alternatively, it is possible to deposit an HfO2 etching barrier layer directly on the guides, or on the several nanometers of silicon oxide previously deposited, then to deposit 550 nm of silicon oxide, for example, which will serve as a sacrificial layer for release by hydrofluoric acid).

A final thin oxide layer 114 measuring 10 nm thick is then deposited, for example by PECVD. (This step is not useful in the aforementioned alternative.)

The surface of the structure 116 thus obtained is planarized and cleaned to prepare it for bonding. The layer 114 serves as a barrier layer during structuring of the MEMS or NEMS.

Figure 8D:
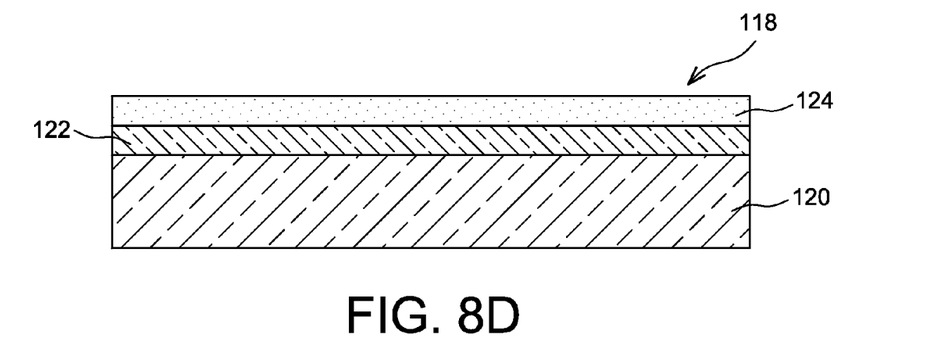
Figure 8E:
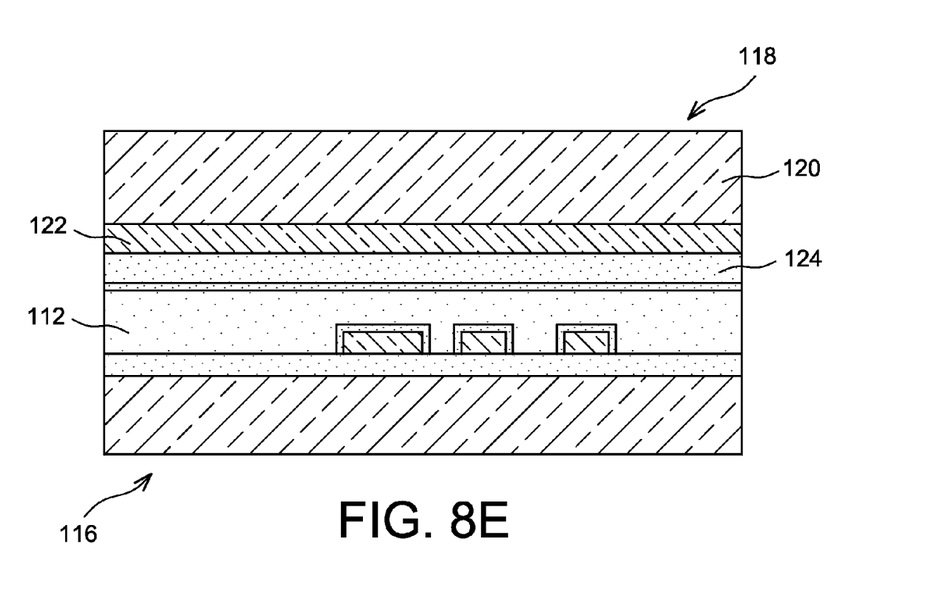
Figure 8F:
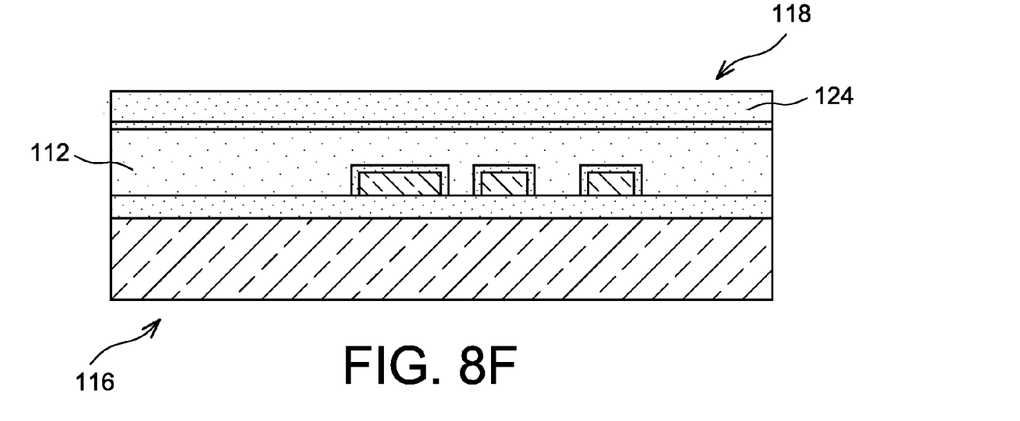

I.3 Bonding of the Upper Layer, Future MEMS or NEMS Layer (FIG. 8D to 8F)

On the surface of the photonic wafer formed by the structure 116, a wafer 118 of the SOI type is bonded, including 500 μm of background Si 120, 400 nm of buried oxide BOX 122, and 200 nm of top silicon 124. The bonding of the wafers 126 and 128 is for example a molecular bonding. It is specified that instead of an SOI-type wafer, it is possible to use an Si wafer that is thinned, then planarized until the desired thickness is obtained.

Next, the resulting structure is thinned, eliminating the entire thickness of silicon 120, i.e., 500 μm, to emerge on the buried oxide (BOX).

The buried oxide 122 is then removed (FIG. 8F), and the top silicon 124 is planarized so as to obtain a desired thickness of approximately from 200 nm to 10 nm. A stack of two wafers is then obtained, with a silicon/oxide interface. Before structuring of the MEMS or NEMS, the configuration of an SOI is thus found: 200 nm of top Si/10 nm of oxide/550 nm of polysilicon.

Figure 8G:
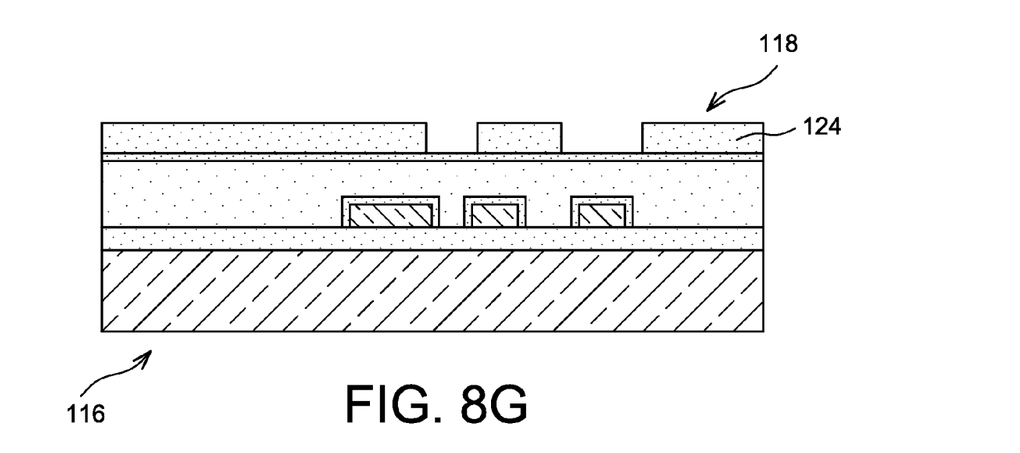
Figure 8H:
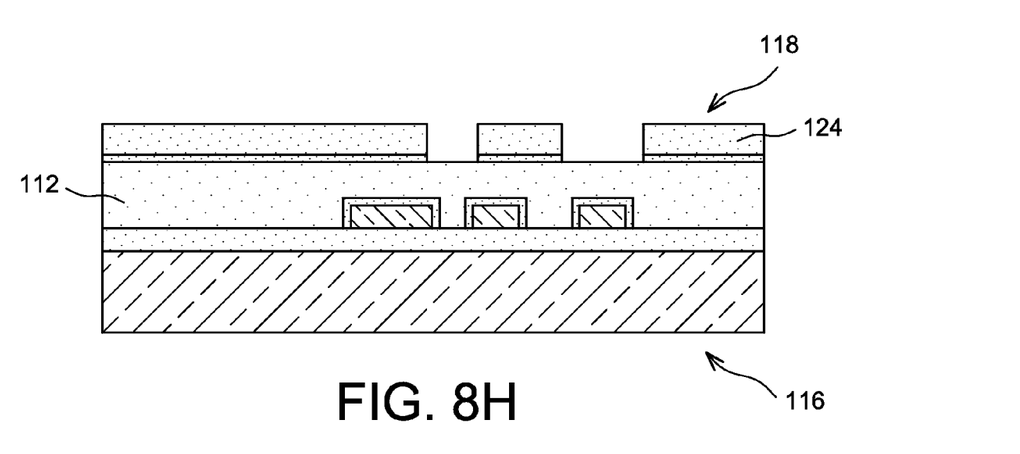
Figure 8I:
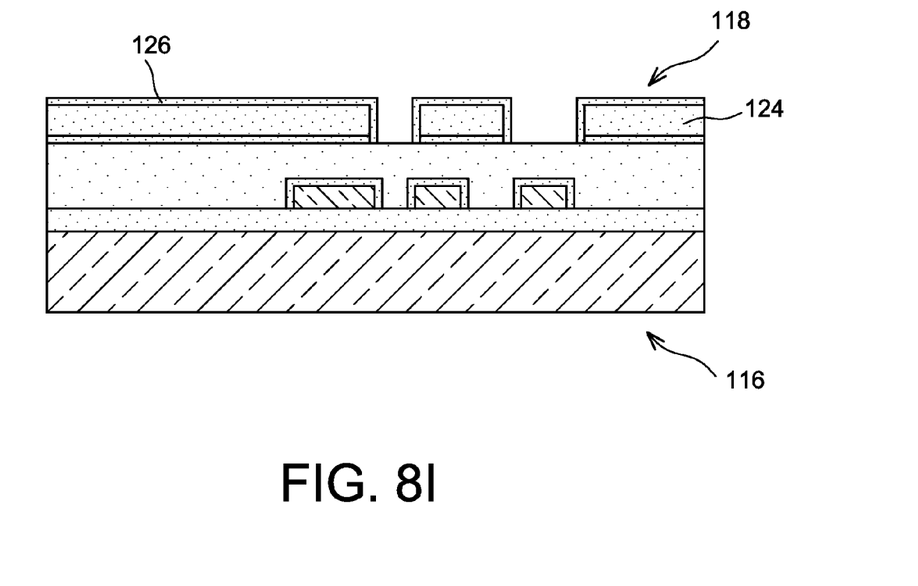

I.4 Structuring of the MEMS or NEMS Arrays (FIGS. 8G to 8I)

Conventional lithography/RIE (reactive ion etching) steps are carried out to structure the MEMS or NEMS in the silicon layer 124 (for example, see the aforementioned article by E. Mile et al.). One then emerges on the oxide layer 112 measuring 10 nm thick. (However, in the aforementioned alternative, one emerges directly on the 550 nm of silicon oxide that serve as the sacrificial layer.)

Next, the MEMS or NEMS are evenly oxidized (FIG. 8I) over a thickness of 10 nm, for example, so as to protect those MEMS or NEMS structures during release of the sacrificial Si layer. The oxide layer resulting therefrom bears reference 126. (In the aforementioned alternative, this step is not necessary.)

The MEMS or NEMS array will have a smaller surface than the photonic circuit so as to allow space for the injection of light using the optical fibers.

A lithography, then an etching of the oxide (10 nm+10 nm) by RIE (anisotropic etching) are then carried out on the areas that must be released. (In the aforementioned alternative, this step is not necessary.)

Figure 8J:
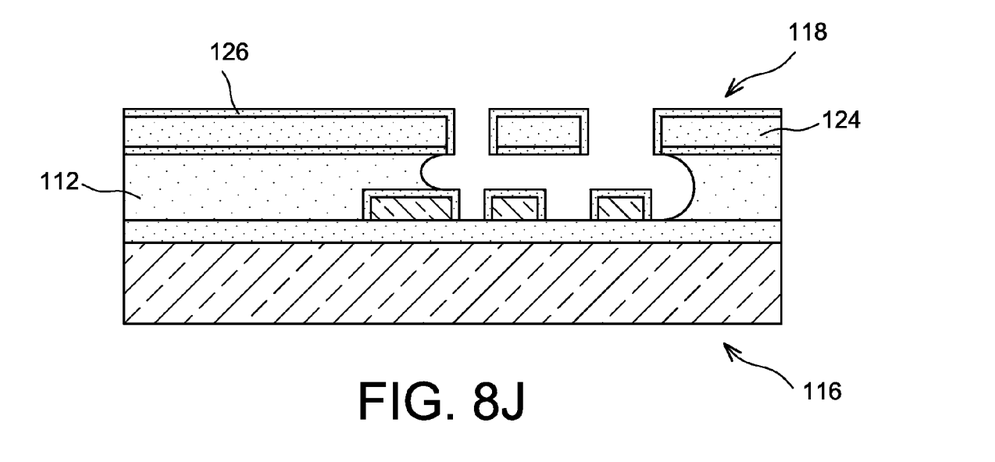

I.5 Release of the Moving Structures (FIG. 8J)

The MEMS or NEMS structures are freed by anisotropic etching of the polycrystalline silicon using $XeF_2$. (In the aforementioned alternative, another method is used: it is freed using hydrofluoric acid, by etching the 550 nm of silicon oxide and stopping on the $HfO_2$).

Suspended MEMS or NEMS structures are ultimately obtained, made up of 10 nm of oxide/200 nm to 50 nm of Si/20 nm of oxide, above silicon waveguides, coated with a layer of oxide whereof the thickness is comprised between 5 nm and 10 nm, and is for example equal to 10 nm.

II. Second Example of a Manufacturing Method (FIGS. 9A to 9E)

The difference between this second example and the first lies in the bonding of the MEMS or NEMS wafer on the photonic wafer while preserving the raised portion (bonding on cavities).

The photonic circuit stays the same. However, for the design thereof, it is advantageously possible to provide large bonding surfaces. The bonding of one wafer to the other is done directly, for example by molecular bonding. The wafers supporting the future MEMS or NEMS are made from silicon and covered with an oxide that will constitute both the bonding interface and the sacrificial layer.

Figure 9A:
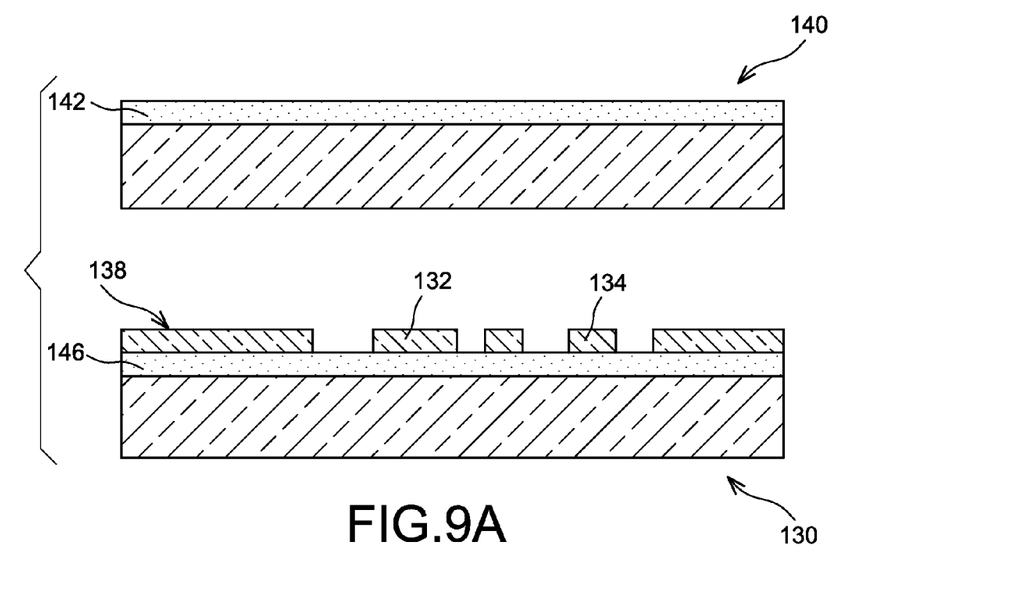

In FIG. 9A, the wafer 130 is shown supporting a waveguide 132 and an optical ring 134. The latter rest on the silica layer 136 included by the wafer 130.

One also sees the silicon wafer 140. It is provided with a superficial layer of silica 142 that is obtained by PECVD and has a thickness of approximately from 10 nm to 500 nm, for example. This layer 142 will serve as a sacrificial layer, fixing the interval between the optical resonator and the MEMS or NEMS structure.

Figure 9B:
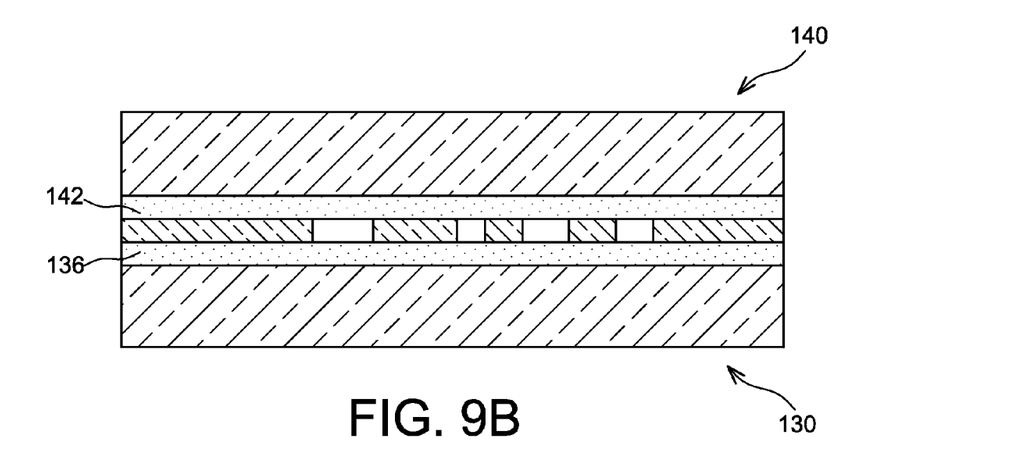
Figure 9C:
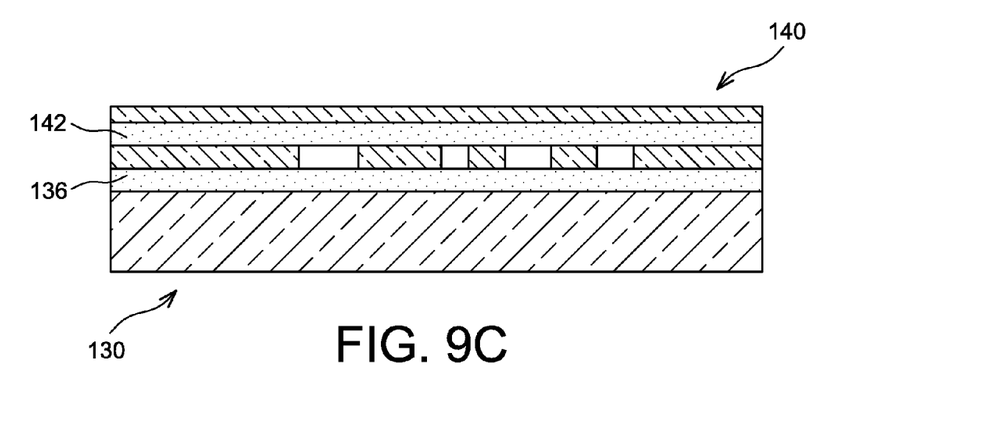
Figure 9D:
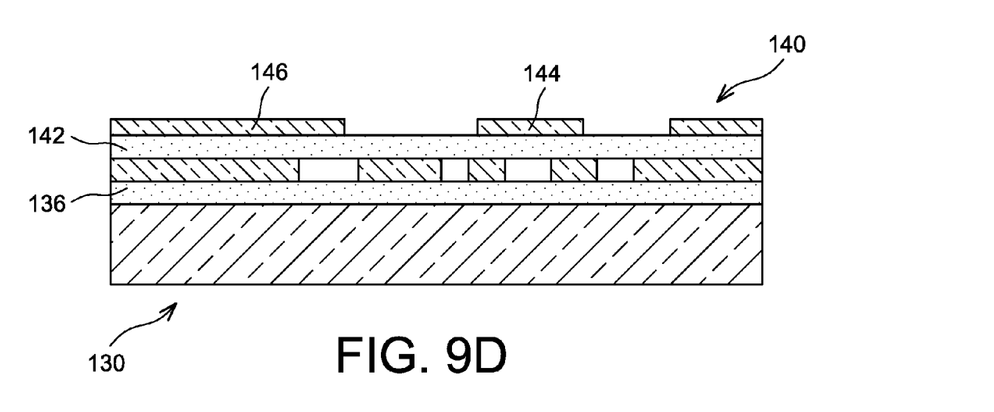
Figure 9E:
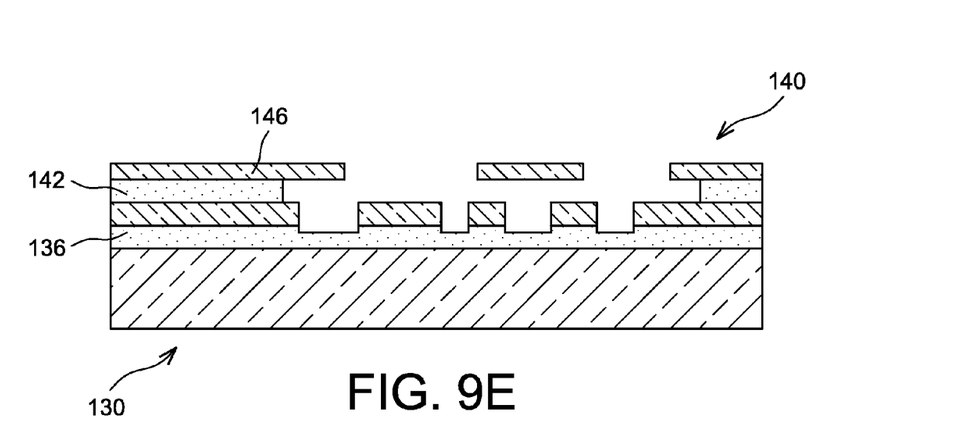

FIG. 9B shows the wafers 130 and 140 bonded to each other. The layer 142 of the wafer 140 is then bonded to the surface of the wafer 130, which bears reference 138 in FIG. 9A.

Next (FIG. 9C), the wafer 140 is thinned, by physicochemical milling, then a final planarization (polishing) is done to obtain the desired thickness, comprised between 10 nm and 200 nm.

The MEMS or NEMS are then structured (FIG. 9D) by lithography/etching. Reference 144 designates these MEMS or NEMS, and reference 146 designates the mechanical support thereof.

It then suffices (FIG. 9E) to perform a release by HF vapor etching, for example. In the illustrated example, the oxide located below the photonic circuit will be slightly etched during the release. This can be controlled in different ways: the oxide of the sacrificial layer is less dense than the thermal oxide placed below the photonic circuit and therefore etches more quickly than the latter. It is also possible to perform a prior anisotropic etching of the silicon oxide so as to limit the HF isotropic etching time.

III. Third Example of a Manufacturing Method

From the perspective of the manufacturing method, the two standard "photonic circuit on silicon" and "MEMS or NEMS on silicon" methods may be combined:

The base wafer may be an SOI wafer for example including a top layer 220 nm thick and a layer of BOX 2 μm thick.

A first lithography/etching cycle makes it possible to model the waveguides and optical resonators in the top layer of the SOI wafer, as well as the coupling arrays, necessary for the connection with optical fibers intended to connect the optomechanical device to a laser and photodetection means.

An $SiO_2$ deposition is then done, for example 500 nm thick.

A planarization is then done by CMP (chemical mechanical polishing), and that CMP is stopped to define the vertical optical interval between the optical resonators and the mechanical resonators.

A barrier layer is next deposited, for example a layer of $HfO_2$ that is 20 nm thick, to prevent the release of the mechanical structure from also leading to freeing the optical guides and optical resonators.

A lithography/etching cycle is carried out to open the barrier layer/oxide stack and model the anchorings for the future mechanical structures.

A layer of material is deposited in which one wishes to form the mechanical structures. This is for example a layer of polycrystalline silicon 100 nm thick.

A lithography/etching cycle is carried out for the preceding layer to define the mechanical resonators.

Then the mechanical structures are freed, for example using HF vapor etching.

The optomechanical devices according to the invention, previously described, include resonant mechanical elements. However, the invention is not limited to such cases: an optomechanical device according to the invention may use one or more non-resonant mechanical elements, for example to detect a force such as a cellular force. In that case, the optomechanical device does not use any actuating device for the mechanical elements, but only a device for detecting movement of the elements, using an optical wave, as seen above.

In the invention, the mechanical elements may be proof masses, vibrating beams or vibrating plates. And at least two ends of each mechanical element may be anchored to the support thereof.

Figure 10:
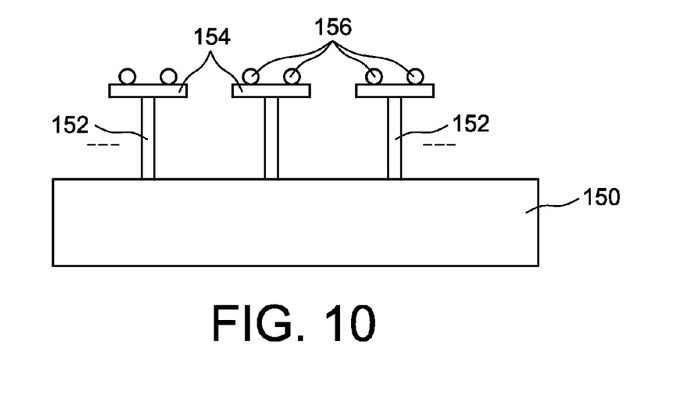
FIG. 10 is a diagrammatic partial cross-sectional view of another example of the device covered by the invention.

In another example of the device covered by the invention, diagrammatically illustrated by FIG. 10, each mechanical element 150 comprises a rectilinear beam 152, perpendicular to the substrate of the device, and having one end anchored to the substrate. The other end of the beam is provided with a flat plate 154, perpendicular to the beam 152 and making up a receiving area, able to receive particles 156 that are capable of causing or modifying the movement of the mechanical element in order to determine a physical property of the particles, for example the mass thereof.

The manufacture of the rectilinear beams on the support may be done for example by using a masking technique on the support and a growth technique for this type of patterns in the openings of the mask.

It is specified that, according to one particular use of the invention, the mechanical elements are capable of receiving an outside flow, for example of the electromagnetic type (thermal and/or optical flow), or one or more particles. Thus, for example, the receiving areas of the flow(s) or the particle(s) are formed by the plate-shaped elements 13 in the case of FIG. 3C,
by beam-shaped elements 34 in the case of FIG. 4, and
by the plates 154 in the case of FIG. 10.

This or these flow(s) or this or these particle(s) are capable of causing or modifying the movement of the mechanical elements in order to determine a physical property of said flow(s) or said particle(s).

The invention claimed is:

1. An optomechanical device, comprising:
a support, and including on the support:
an array of mechanical elements anchored to the support and configured to move with respect to the support; and
an actuating and/or detecting device, configured to actuate mechanical elements of the array and/or to detect movement of the mechanical elements or frequency variations of the movement, said device being disposed in vicinity of at least some of the mechanical elements and between the mechanical elements and the support, said device comprising a photonic circuit including an array of optical filters, a number of optical filters of the array being less than or equal to a number of the mechanical elements,
wherein each optical filter of the array is configured to resonate at a particular wavelength and is optically coupled to one of the mechanical elements to actuate the mechanical elements and/or to detect the movement of the mechanical elements or the frequency variations of the movement independently of one another,
wherein the optical filters are fixed with respect to the support, and
wherein the mechanical elements and the optical filters are superimposed.

2. The optomechanical device according to claim 1, wherein each mechanical element of the array includes at least two ends that are anchored to the support.

3. The optomechanical device according to claim 1, wherein the actuating and/or detecting device is positioned below or above all or some of the mechanical elements, between the mechanical elements and the support.

4. The optomechanical device according to claim 1, wherein the optical filters are optical resonators.

5. The optomechanical device according to claim 4, wherein the optical resonators are chosen from among annular optical resonators, discoid optical resonators, or photonic crystals.

6. The optomechanical device according to claim 4, wherein the photonic circuit further includes at least one optical waveguide that extends across from the optical resonators and is placed at a small enough distance therefrom to allow optical interactions between them.

7. The optomechanical device according to claim 6, wherein the distance is from 10 nm to 1 µm.

8. The optomechanical device according to claim 1, wherein the actuating and/or detecting device comprises a device configured to electrically actuate the mechanical elements.

9. The optomechanical device according to claim 1, wherein the mechanical elements are mechanically resonant elements.

10. The optomechanical device according to claim 1, wherein the mechanical elements are chosen from among proof masses, vibrating beams, or vibrating plates.

11. The optomechanical device according to claim 1, wherein each mechanical element of the array comprises a substantially rectilinear beam, perpendicular to the support and including first and second ends, the first end being anchored to the support.

12. The optomechanical device according to claim 11, wherein the second end of the beam includes a substantially planar plate, perpendicular to the beam and forming a receiving area.

* * * * *